United States Patent
Guala

(10) Patent No.: US 8,652,109 B2
(45) Date of Patent: Feb. 18, 2014

(54) SYRINGE WITH INTEGRATED VALVE MALE LUER LOCK CONNECTOR

(75) Inventor: Gianni Guala, Turin (IT)

(73) Assignee: Industrie Borla S.p.A., Moncalieri (Turin) (IT)

( * ) Notice: Subject to any disclaimer, the term of this patent is extended or adjusted under 35 U.S.C. 154(b) by 272 days.

(21) Appl. No.: 12/742,803

(22) PCT Filed: Nov. 12, 2008

(86) PCT No.: PCT/IB2008/003168
§ 371 (c)(1),
(2), (4) Date: Aug. 26, 2010

(87) PCT Pub. No.: WO2009/063313
PCT Pub. Date: May 22, 2009

(65) Prior Publication Data
US 2010/0324502 A1  Dec. 23, 2010

(30) Foreign Application Priority Data
Nov. 14, 2007 (IT) .............................. TO20070141 U

(51) Int. Cl.
*A61M 5/315* (2006.01)
*A61M 5/00* (2006.01)

(52) U.S. Cl.
USPC ............ 604/236; 604/187; 604/218; 604/905

(58) Field of Classification Search
USPC ......... 604/187, 218, 222, 236, 237, 240, 241, 604/257, 263, 905
See application file for complete search history.

(56) References Cited

U.S. PATENT DOCUMENTS 5,484,070 A * 1/1996 Graham ........................ 215/223
6,106,502 A   8/2000 Richmond
6,932,795 B2 * 8/2005 Lopez et al. .................. 604/249

FOREIGN PATENT DOCUMENTS

| EP | 1 747 796 | 1/2007 |
| GB | 1 448 108 | 9/1976 |
| WO | WO 2004/060474 | 7/2004 |
| WO | WO 2005/065767 | 7/2005 |
| WO | WO 2006/074935 | 7/2006 |

OTHER PUBLICATIONS

International Search Report for PCT/IB2008/003168, mailed May 29, 2009.
Written Opinion for PCT/IB2008/003168, mailed May 29, 2009.

* cited by examiner

*Primary Examiner* — Theodore Stigell
*Assistant Examiner* — Leah Stohr
(74) *Attorney, Agent, or Firm* — Nixon & Vanderhye P.C.

(57) ABSTRACT

Syringe (1) including a cylinder (2) and a piston (4), in which the outlet end (6) of the cylinder (2) is integrated with a valve male luer lock connector (7).

2 Claims, 1 Drawing Sheet

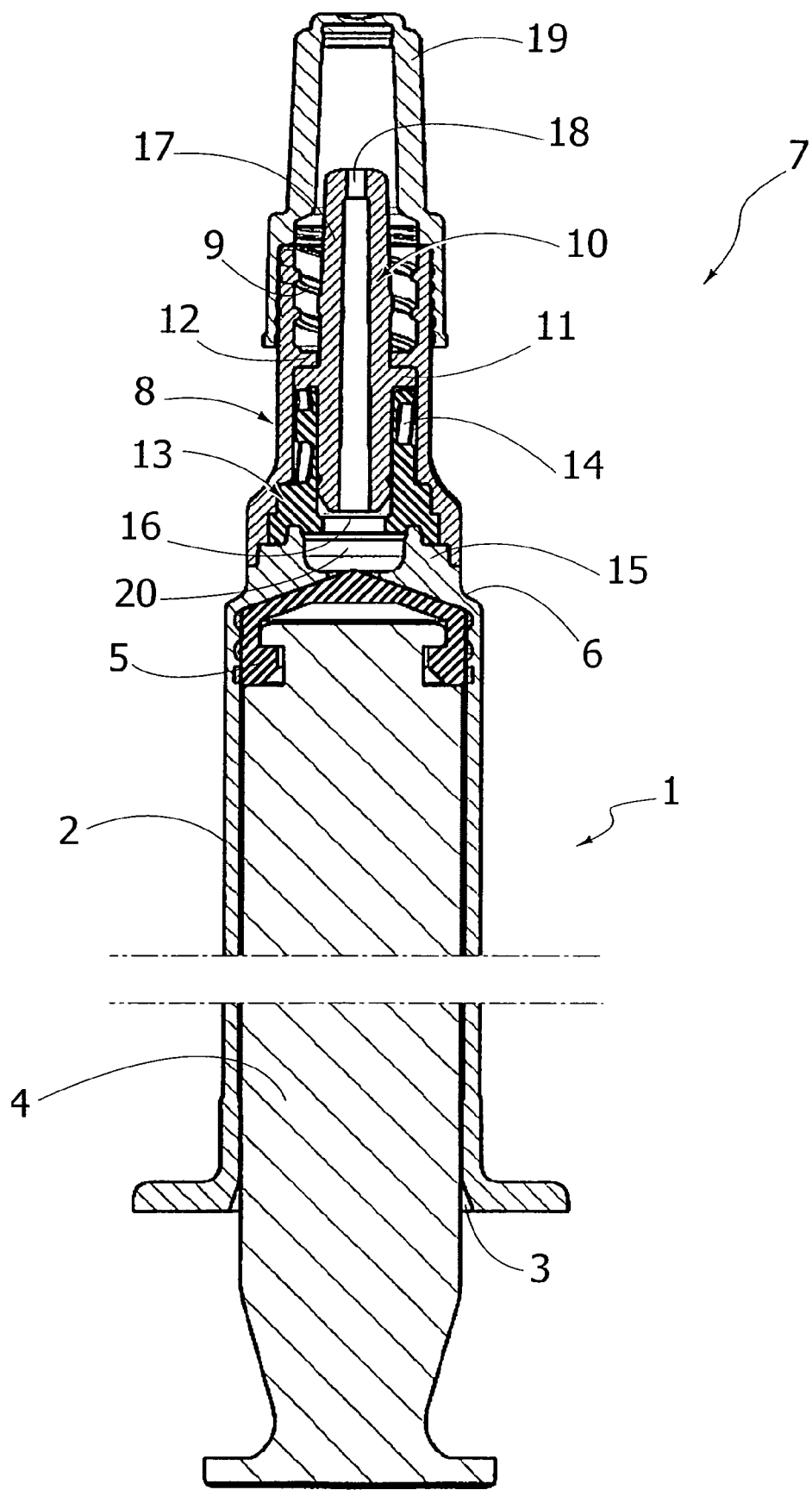

SYRINGE WITH INTEGRATED VALVE MALE LUER LOCK CONNECTOR

This application is the U.S. national phase of International Application No. PCT/IB2008/003168 filed 12 Nov. 2008 which designated the U.S. and claims priority to IT Patent Application No. TO2007U000141 filed 14 Nov. 2007, the entire contents of each of which are hereby incorporated by reference.

FIELD OF THE INVENTION

The present invention refers to syringes for medical use including a cylinder and a piston sealingly sliding inside the cylinder for injecting a fluid through an outlet end of the cylinder.

STATE OF THE PRIOR ART

Syringes thus made are typically used for introducing medications into a parenteral fluid of an infusion line and the like. The outlet end of the syringe cylinder is generally designed to be connected to a connector, typically a luer connector, through which the medical fluid previously suctioned into the syringe cylinder is then injected into the infusion line.

Applications thus made have the necessity to avoid any contamination of the fluid contained in the syringe, before being injected.

SUMMARY OF THE INVENTION

The object of the present invention is that of providing an efficient and practical solution to the abovementioned need, both in terms of anti-contamination safety and comfort for the operator when connecting the syringe to the medical line.

According to the invention this object is attained by virtue of the fact that the abovementioned outlet end of the syringe cylinder is integrated with a luer connector or a valve male luer lock connector.

The integrated valve connector can be advantageously of the type described and illustrated in the European patent application EP-A-1 747 796 in the name of the same Applicant.

BRIEF DESCRIPTION OF THE DRAWING

Now, the invention shall be described in detail with reference to the attached drawing, strictly provided by way of non-limiting example, schematically showing—in longitudinal section—a syringe with an integrated valve connector according to the invention.

DETAILED DESCRIPTION OF THE INVENTION

In the drawing, indicated in its entirety with 1 is a syringe according to the invention, with or without a needle, comprising an elongated cylinder 2 with an open end 3 inserted inside which is an axially sliding piston 4 provided with an end gasket 5 in sliding sealing contact with the internal wall of the cylinder 2.

The other end of the cylinder 2, indicated by 6, is in communication with a valve connector 7, integrated with the cylinder 2.

The valve connector 7, of the luer or male luer lock type, generally corresponds to the one described and illustrated in the aforementioned European patent application EP-A-1 747 796. In detail, it comprises a hollow body 8 permanently and rigidly fixed to the end 6 of the cylinder 2 on one side and it is formed with an internal threading 9 on the opposite side. Axially sliding inside the body 8 is an internal tubular body 10 made, approximately at its median section, with an annular flange 11 coupled in a non-rotating manner with the internal wall of the body 8 and normally arranged lying against an internal annular stop collar 12 integrally made with the body 8. This position is usually maintained due to the action of a hollow body made of elastic material 13 formed with an axially elastically yielding wall portion 14, bearing against an annular flange 11 of the internal tubular element 10, interposed between the body 8 and the end 6 of the cylinder 2. The body of elastic material 13 is arranged in frontal sealing contact against a step annular relief 15 of the end 6 of the cylinder 2, which delimits a cavity 20.

The portion of the internal tubular element 10 comprised between the annular flange 11 and the cylinder 2 sealingly slides inside the body of plastic material 13, and the related free end faces a pre-cutting 16 of the latter, usually hermetically sealed due to the effect of a suitable radial preload between such elastic body 13 and the body 8 of the connector 7.

The body of elastic material 13 integrates three functions: a first function, as mentioned, for pushing the internal tubular element 10 in the retracted position represented in the figure, in which the annular flange 11 bears against the internal collar 12 and the valve connector 7 is in a hermetically sealed state.

A second sliding sealing function between the internal tubular element 10 and the body 8, and a third function consisting of defining a flow passage through the pre-cutting 16 in the open state of the connector 7, according to the mode clarified hereinafter.

The tubular element 10 extends, at the opposite part with respect to the elastic body 13, through the internal threading 9 of the body 8 with a portion having a cone-shaped external surface 17, in such a manner to define a male luer lock fitting therewith, couplable with a supplementary female luer lock fitting of a medical line. Such cone-shaped surface portion 17 ends with a narrow internal passage 18.

A protection cap 19 is engaged in a removable manner on the end part of the body 8.

As clarified previously, the drawing represents the closed state of the connector 7 integrated with the cylinder 2 of the syringe 1. In such state, the flow passage from the end 6 of the cylinder 2 towards the internal tubular element 10 is hindered, i.e. occluded in a sealed manner, by the elastic body 13 whose pre-cutting 16 remains hermetically sealed. When a female luer lock fitting is engaged with the connector 7, being screwed into the internal threading 9 of the body 8, the internal tubular element 10 is translated axially in the direction of the cylinder 2, moving forward against the elastic body 13 up to opening the pre-cutting 16. In such manner, the flow passage between the cylinder 2 and the female luer lock fitting is opened, through the internal tubular element 10 and the relative narrow passage 18. In this step, the elastically yielding part 14 of the elastic body 13 is compressed in a spring-like manner.

When—after completing injecting the fluid contained in the cylinder 2 operated by means of the piston 4—the female luer lock fitting is unscrewed and removed, the internal tubular element 10 returns to the initial retracted position, due to the springback effect of the elastically yielding part 14 of the elastic body 13 in its initial state. Therefore, its annular flange 11 returns to the position against the collar 12 and the pre-cutting 16 is again hermetically closed, thus sealing the syringe 1 again.

Obviously, the construction details and the embodiments may widely vary with respect to the description and illustration provided above, without for this reason departing from the scope of the invention as defined by the following claims.

Thus, for example, the valve connector 7 integrated with the syringe 1 may also be of a different configuration with respect to the one described, i.e. different with respect to the one according to document EP-A-1 747 796, as long as it is suitable to attain the same functional effects.

The invention claimed is:

1. A syringe comprising a cylinder and a piston sealingly sliding inside said cylinder for injecting a fluid through an outlet end of said cylinder, wherein said outlet end of said cylinder is integrated with a valve male luer lock connector comprising an outer hollow body, an internal tubular element axially slidable inside the outer body, and a tubular body of elastic material defining a flow passage in an open state of said connector, wherein the tubular body of elastic material comprises an axially elastically yielding wall portion for providing a sliding seal between the internal tubular element and the outer body and for pushing the internal tubular element in a position corresponding to a hermetically sealed state of said connector, and wherein said outlet end of said cylinder has a step annular relief, said step annular relief comprising an annular outer step permanently fixed to said outer body of said luer lock connector and an annular inner step arranged in frontal sealing contact against said tubular body of elastic material, said annular inner step delimiting a cavity facing said flow passage.

2. The syringe according to claim 1, wherein said connector is provided with a removable protection cap.

* * * * *